United States Patent
Someda et al.

(10) Patent No.: US 8,997,571 B2
(45) Date of Patent: Apr. 7, 2015

(54) ULTRASONIC PROBE, AND PHOTOACOUSTIC-ULTRASONIC SYSTEM AND INSPECTION OBJECT IMAGING APPARATUS INCLUDING THE ULTRASONIC PROBE

(75) Inventors: Yasuhiro Someda, Yokohama (JP); Keishi Saito, Tokyo (JP); Yasufumi Asao, Atsugi (JP); Katsumi Nakagawa, Yokohama (JP); Shigeru Ichihara, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 325 days.

(21) Appl. No.: 12/999,303

(22) PCT Filed: Jun. 17, 2009

(86) PCT No.: PCT/JP2009/061434
§ 371 (c)(1),
(2), (4) Date: Dec. 15, 2010

(87) PCT Pub. No.: WO2009/154298
PCT Pub. Date: Dec. 23, 2009

(65) Prior Publication Data
US 2011/0088477 A1    Apr. 21, 2011

(30) Foreign Application Priority Data

Jun. 18, 2008 (JP) .................................. 2008-159314
Jun. 5, 2009 (JP) .................................. 2009-136365

(51) Int. Cl.
*A61B 5/05* (2006.01)
*G01N 23/02* (2006.01)
(Continued)

(52) U.S. Cl.
CPC ................. *A61B 8/14* (2013.01); *A61B 5/0095* (2013.01); *A61B 8/5238* (2013.01); *A61B 8/0825* (2013.01)

(58) Field of Classification Search
USPC ............................ 73/579, 584, 596, 609–629
See application file for complete search history.

(56) References Cited

U.S. PATENT DOCUMENTS 3,881,164 A * 4/1975 Kossoff ......................... 367/138
4,242,912 A * 1/1981 Burckhardt et al. ............ 73/626
(Continued)

FOREIGN PATENT DOCUMENTS

CN    1575770 A    2/2005
CN    1650794 A    8/2005
(Continued)

OTHER PUBLICATIONS

Zhuang et al., "Two-dimensional Capacitive Micromachined Ultrasonic Transducer (CMUT) Arrays for a Miniature Integrated Volumetric Ultrasonic Imaging System", Medical Imaging 2005: Ultrasonic Imaging and Signal Processing, Proceedings of the SPIE, vol. 5750, pp. 37-46.*
(Continued)

*Primary Examiner* — David A Rogers
(74) *Attorney, Agent, or Firm* — Canon USA Inc. IP Division (57) ABSTRACT

Provided are an ultrasonic probe capable of forming an image without degradation even when the frequency band of a photoacoustic wave and the frequency band of an ultrasonic wave used in ultrasonography are separated from each other, and an inspection object imaging apparatus including the ultrasonic probe. The ultrasonic probe includes a first array device capable of transmitting and receiving an ultrasonic wave; and a second array device capable of receiving a photoacoustic wave. The first array device includes plural electromechanical transducers arranged in a direction perpendicular to a scanning direction, the second array device includes plural electromechanical transducers arranged in a two-dimensional manner, and the first array device and the second array device are provided on the same plane and in the scanning direction.

20 Claims, 5 Drawing Sheets (51) Int. Cl.
*A61B 8/14* (2006.01)
*A61B 5/00* (2006.01)
*A61B 8/08* (2006.01)

(56) References Cited

U.S. PATENT DOCUMENTS

| | | | | |
|---|---|---|---|---|
| 4,570,488 | A * | 2/1986 | Miwa et al. | 73/626 |
| 4,831,601 | A | 5/1989 | Breimesser et al. | |
| 4,870,867 | A * | 10/1989 | Shaulov | 73/625 |
| 6,278,224 | B1 * | 8/2001 | Sawada et al. | 310/334 |
| 6,524,254 | B2 * | 2/2003 | Erikson | 600/447 |
| 6,915,696 | B2 * | 7/2005 | Dufait et al. | 73/626 |
| 7,066,887 | B2 * | 6/2006 | Flesch et al. | 600/447 |
| 7,886,605 | B2 * | 2/2011 | Malin et al. | 73/644 |
| 7,963,919 | B2 * | 6/2011 | Proulx et al. | 600/447 |
| 8,070,682 | B2 * | 12/2011 | Zhu | 600/437 |
| 8,121,663 | B2 * | 2/2012 | Peyman et al. | 600/319 |
| 8,239,006 | B2 * | 8/2012 | Zhu et al. | 600/475 |
| 8,286,488 | B2 * | 10/2012 | Meyer et al. | 73/600 |
| 2002/0035327 | A1 | 3/2002 | Kruger | |
| 2002/0050169 | A1 * | 5/2002 | Ritter et al. | 73/606 |
| 2003/0024317 | A1 * | 2/2003 | Miller | 73/643 |
| 2003/0167002 | A1 * | 9/2003 | Nagar et al. | 600/437 |
| 2004/0215072 | A1 * | 10/2004 | Zhu | 600/407 |
| 2005/0004458 | A1 | 1/2005 | Kanayama et al. | |
| 2005/0187471 | A1 | 8/2005 | Kanayama et al. | |
| 2007/0287912 | A1 * | 12/2007 | Khuri-Yakub et al. | 600/439 |
| 2008/0033262 | A1 * | 2/2008 | Peyman et al. | 600/319 |
| 2008/0058638 | A1 * | 3/2008 | Zhu et al. | 600/425 |
| 2008/0071172 | A1 | 3/2008 | Bruck et al. | |
| 2008/0134793 | A1 * | 6/2008 | Woychik et al. | 73/649 |
| 2008/0196506 | A1 * | 8/2008 | Satoh et al. | 73/629 |
| 2008/0314153 | A1 * | 12/2008 | Langlois et al. | 73/606 |
| 2009/0171213 | A1 * | 7/2009 | Savord | 600/447 |
| 2010/0256496 | A1 * | 10/2010 | Zhu | 600/459 |
| 2011/0066023 | A1 * | 3/2011 | Kanayama et al. | 600/407 |
| 2012/0259205 | A1 * | 10/2012 | Peyman | 600/420 |

FOREIGN PATENT DOCUMENTS

| | | |
|---|---|---|
| JP | 63121749 A | 5/1988 |
| JP | 4138146 A | 5/1992 |
| JP | 2001507952 T | 6/2001 |
| JP | 2004-274721 A | 9/2004 |
| JP | 2005021380 A | 1/2005 |
| JP | 2007-502189 A | 2/2007 |
| JP | 2007244415 A | 9/2007 |
| JP | 2007-319553 A | 12/2007 |
| JP | 2010-022816 A | 2/2010 |
| WO | 2007/148239 A2 | 12/2007 |
| WO | 2007148239 A2 | 12/2007 |
| WO | 2008054395 A1 | 5/2008 |

OTHER PUBLICATIONS

Niederhauser et al., "Combined Ultrasound and Optoacoustic System for Real-Time High-Contrast Vascular Imaging in Vivo", IEEE Transactions on Medical Imaging, Apr. 2005, pp. 436-440, vol. 24, No. 4.

Niederhauser et al., "Combined Ultrasound and Optoacoustic System for Real-Time High-Contrast Vascular Imaging in Vivo", IEEE Transactions on Medical Imaging, Apr. 2005; vol. 24, No. 4, pp. 436-440.

Kozhushko et al., "Focused Array Transducer for Two-Dimensional Optoacoustic Tomography", The Journal of the Acoustical Society of America, Sep. 2004, vol. 116, No. 3, pp. 1498-1506.

Wygant et al., "Photoacoustic Imaging Using a Two-Dimensional CMUT Array", IEEE Ultrasonics Symposium, 2005, pp. 1921-1924.

* cited by examiner

ULTRASONIC PROBE, AND PHOTOACOUSTIC-ULTRASONIC SYSTEM AND INSPECTION OBJECT IMAGING APPARATUS INCLUDING THE ULTRASONIC PROBE

TECHNICAL FIELD

The present invention relates to an ultrasonic probe for transmitting and receiving an ultrasonic wave and for receiving a photoacoustic wave, and to a photoacoustic-ultrasonic system and an inspection object imaging apparatus including the ultrasonic probe.

BACKGROUND ART

A conventional tomographic imaging apparatus which obtains a tomographic image using an ultrasonic wave includes: a probe for transmitting an ultrasonic wave to a sample and receiving the reflected ultrasonic wave; a transmitting portion for supplying an ultrasonic signal to the probe; a receiving portion for receiving the reflected wave; and a unit for converting the received reflected wave signal into a luminance signal for visualization. When a time-series tomographic image acquired by the apparatus is used, it is possible to observe an inside of a sample. In the apparatus according to one mode, a unit for performing scanning of a probe two-dimensionally scans a sample with an ultrasonic wave to obtain a three-dimensional image.

Meanwhile, in examining an inspection object, apparatuses which display not only a morphologic image but also a functional image have progressively been developed in recent years. As one of such apparatuses as described above, there is an apparatus which utilizes a photoacoustic spectroscopy. In the photoacoustic spectroscopy, visible light, near-infrared light, or mid-infrared light each having a predetermined wavelength is applied to the inspection object. Then, a specific substance inside the inspection object absorbs energy of the applied light, and as a result of the absorption, an elastic wave (photoacoustic wave) is generated and detected. In this manner, concentration of the specific substance is quantitatively measured. The specific substance inside the inspection object is, for example, glucose or hemoglobin contained in blood. A technology of acquiring a photoacoustic image through the photoacoustic spectroscopy is disclosed in, for example, Japanese Patent Application Laid-Open No. 2001-507952. The technology is referred to as a photoacoustic tomography (PAT).

In addition, Japanese Patent Application Laid-Open No. 2005-021380 discloses a method of reconstructing both a photoacoustic image and a normal ultrasonic echo image using a one-dimensionally-arranged electromechanical transducer which is common to the both images; and a structure in which a lighting system using a glass fiber is provided between one-dimensionally-arranged electromechanical transducers. According to Japanese Patent Application Laid-Open No. 2005-021380, the ultrasonic echo image and the photoacoustic image are simultaneously acquired, thereby displaying a morphologic image and a functional image. In this case, a common probe is used to transmit and receive an ultrasonic wave for forming the ultrasonic echo image and to receive a photoacoustic wave for forming the photoacoustic image.

It should be noted herein that an elastic wave generated by the photoacoustic spectroscopy (photoacoustic imaging method) is referred to as a photoacoustic wave, and a sonic wave which is transmitted and received in a normal pulse echo method is referred to as an ultrasonic wave.

The frequency band of a photoacoustic wave used in the photoacoustic spectroscopy is generally lower than the frequency band of an ultrasonic wave used in ultrasonography. For example, the frequency band of the photoacoustic wave is distributed within a range of 200 KHz to 2 MHz with 1 MHz being a center frequency. The distribution of the frequency band of the photoacoustic wave is lower than a center frequency of 3.5 MHz of the ultrasonic wave used in ultrasonography. According to Japanese Patent Application Laid-Open No. 2005-021380, the common probe is used to receive the photoacoustic wave and the ultrasonic wave used in ultrasonography.

However, as described in Japanese Patent Application Laid-Open No. 2005-021380, when the common probe is used to receive the photoacoustic wave and the ultrasonic wave which have frequency bands different from each other, there arises a problem that spatial resolution is deteriorated in the ultrasonic image. In order to solve the above-mentioned problem, a harmonic imaging method is used in Japanese Patent Application Laid-Open No. 2005-021380. However, a signal contained in a harmonic component is attenuated more than a signal contained in a fundamental component, and hence there is a fear that sensitivity may be decreased.

In a case where the frequency band of the photoacoustic wave and the frequency band of the ultrasonic wave are remarkably separated from each other (for example, the center frequency band of the photoacoustic wave is approximately 1 MHz and the center frequency band of the ultrasonic wave is approximately 10 MHz), the above-mentioned problem becomes more remarkable when the common probe is used to receive the waves as described in Japanese Patent Application Laid-Open No. 2005-021380.

Moreover, with regard to a photoacoustic-ultrasonic system including an ultrasonic probe and an optical system, the following problem arises. Specifically, according to Japanese Patent Application Laid-Open No. 2005-021380, for generation of a photoacoustic wave, a laser light is introduced using an optical fiber. However, in order to generate the photoacoustic wave, an extremely strong laser light is required, which may adversely affect the fiber. Particularly, when a sample is thick so that light is attenuated to a large degree, the above-mentioned problem becomes more serious.

According to an experiment conducted by the inventors of the present invention using a dummy inspection object, it was found that, in order to generate a photoacoustic wave strong enough to detect a sample having a thickness exceeding the order of "cm", the intensity of the laser light introduced into the optical fiber exceeds several tens $kJ/cm^2$, which increases a burden on the optical fiber. Therefore, the optical fiber may not be selected as the optical system for detecting a sample having a certain volume.

DISCLOSURE OF THE INVENTION

An object of the present invention is to provide an ultrasonic probe capable of forming an image without degradation even when a frequency band of a photoacoustic wave and a frequency band of an ultrasonic wave used in ultrasonograpy are separated from each other, and an inspection object imaging apparatus including the ultrasonic probe.

Another object of the present invention is to provide a photoacoustic-ultrasonic system including the ultrasonic probe and an optical system, which is capable of applying pulse light having a strong light intensity for detecting a sufficient photoacoustic wave.

In view of the above-mentioned objects, the present invention provides an ultrasonic probe, comprising: a first array device capable of transmitting and receiving an ultrasonic wave; and a second array device capable of receiving a photoacoustic wave, wherein the first array device includes plural electromechanical transducers arranged in a first direction; the second array device includes plural electromechanical transducers arranged two-dimensionally; and the first array device and the second array device are provided on the same plane and in a second direction perpendicular to the first direction.

The present invention also provides a photoacoustic-ultrasonic system, comprising: an optical system for introducing light emitted from a light source into an inspection object; and the ultrasonic probe, wherein the optical system is provided in an interspace between the first array device and the second array device.

The present invention also provides an inspection object imaging apparatus, comprising: a light source for generating pulse light; the ultrasonic probe; and a system control unit for controlling the light source and the ultrasonic probe to form an image. The system control unit forms an image based on morphologic information inside an inspection object by using the first array device and forms an image based on functional information inside the inspection object by using the light source and the second array device.

According to the present invention, there can be provided an ultrasonic probe capable of forming an image without degradation even when the frequency band of the photoacoustic wave and the frequency band of the ultrasonic wave used in ultrasonography are separated from each other, and an inspection object imaging apparatus including the ultrasonic probe.

Other features and advantages of the present invention will be apparent from the following description taken in conjunction with the accompanying drawings, in which like reference characters designate the same or similar parts throughout the figures thereof.

BEST MODE FOR CARRYING OUT THE INVENTION

Preferred embodiments of the present invention are now described in detail in accordance with the accompanying drawings.

Hereinafter, the present invention is described in more detail with reference to the accompanying drawings. It should be noted that the same components are denoted by the same reference symbol in general, and description thereof is omitted.

First Embodiment: Ultrasonic Probe and Inspection Object Imaging Apparatus

An ultrasonic probe according to this embodiment includes a first array device capable of transmitting and receiving an ultrasonic wave; and a second array device capable of receiving a photoacoustic wave. The first array device includes plural electromechanical transducers arranged in a first direction. The second array device includes plural electromechanical transducers arranged two-dimensionally. The first array device and the second array device are provided on the same plane and in a second direction. In the present invention, the "same plane" is not necessarily required to be strictly the same plane as long as the plane can be regarded as substantially the same plane. In the definition of "substantially the same plane", it is acceptable that the plane on which the array devices are provided includes irregularities within a range of processing accuracy and includes inclination or level difference as long as the contact condition between an inspection object and the array device is not adversely affected. Even when irregularities or the like are intentionally provided on a surface of the plane in order to reduce contact resistance with the inspection object, similarly to the above-mentioned case, the irregularities or the like are acceptable as long as the contact condition between the inspection object and the array device is not adversely affected.

In the ultrasonic probe and an inspection object imaging apparatus including the ultrasonic probe according to this embodiment, the second direction is typically a scanning direction and the first direction is typically a direction perpendicular to the scanning direction.

The ultrasonic probe and the inspection object imaging apparatus including the ultrasonic probe according to this embodiment may acquire an image of the inspection object even in a rest state without scanning the first array device and the second array device.

Figure 1A:
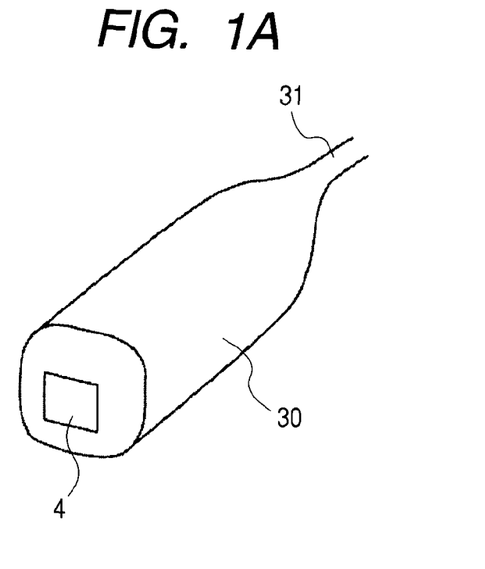
FIG. 1A is a view illustrating an ultrasonic probe according to an embodiment of the present invention.
Figure 1B:
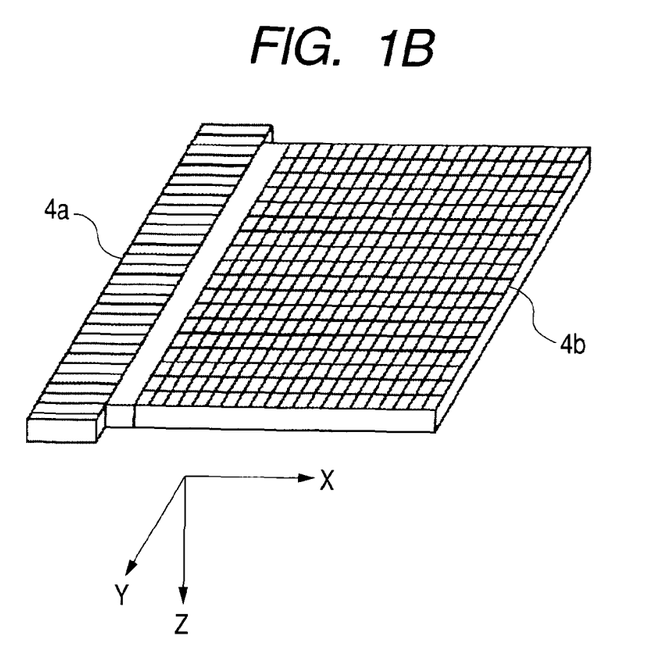
FIG. 1B is a view illustrating an arrangement of an ultrasonic transducer and a photoacoustic transducer which form a transducer used in the ultrasonic probe according to the embodiment of the present invention.

Hereinafter, description is specifically made with reference to the accompanying drawings. FIGS. 1A and 1B are structural views of the ultrasonic probe according to the present invention. FIG. 1A is a schematic view and FIG. 1B is an enlarged view illustrating a transducer portion. The ultrasonic probe includes a probe case 30, a cable 31, and a transducer 4. The transducer 4 is comprised of an ultrasonic transducer 4a which is the first array device capable of transmitting and receiving an ultrasonic wave; and a photoacoustic transducer 4b which is the second array device capable of receiving a photoacoustic wave. A one-dimensional (linear) array is employed for the ultrasonic transducer 4a while a two-dimensional array is employed for the photoacoustic transducer 4b.

The ultrasonic transducer 4a is used for revealing morphologic information of the inside of the inspection object, and therefore is a transducer capable of transmitting and receiving an ultrasonic wave higher in frequency than a photoacoustic wave received by the photoacoustic transducer 4b which acquires functional information. Here, the frequency band of the ultrasonic transducer 4a is 7 to 12 MHz as a typical value. The "morphologic information" is information which is based on a morphology of the inside of the inspection object and obtained by a normal pulse echo method.

On the other hand, the photoacoustic transducer 4b is used for revealing functional information of the inside of the inspection object, and therefore is a transducer capable of receiving an ultrasonic wave (photoacoustic wave) lower in frequency than an ultrasonic wave transmitted and received by the ultrasonic transducer 4a which acquires morphologic information. Here, the frequency band of the photoacoustic transducer 4b is 1 to 4 MHz as a typical value. The "functional information" is information which is obtained by a photoacoustic spectroscopy (photoacoustic imaging method) and relates to concentration of a specific substance inside the inspection object, such as glucose or hemoglobin contained in blood.

The reason why the one-dimensional array is employed for the ultrasonic transducer 4a is as follows. The ultrasonic transducer 4a transmits and receives an ultrasonic wave having a relatively high frequency, and hence the device density thereof needs to be made high. For example, the number of transducer arrays is as large as 128 to 256 even in the one-dimensional array. Therefore, when the two-dimensional array is employed for the ultrasonic transducer 4a, it is not appropriate in terms of costs.

The main reason why the two-dimensional array is employed for the photoacoustic transducer 4b is that light utilization efficiency is regarded as important. Specifically, when photoacoustic waves generated by one irradiation with laser light are received by two-dimensionally-arranged devices, larger number of photoacoustic waves can be received compared with a case where the devices are one-dimensionally arranged. The photoacoustic wave is generally lower in frequency than an ultrasonic echo, and hence the device density can be suppressed to be small. Accordingly, the two-dimensional array has a small influence on costs. The number of transducer arrays in one line is approximately 10 to 50.

The ultrasonic transducer 4a includes the plural electromechanical transducers. The electromechanical transducer is a device which conducts mutual conversion between an electrical signal and a mechanical vibration (ultrasonic wave), and, for example, a piezoelectric device is used therefor. The plural electromechanical transducers are arranged in a direction (first direction) perpendicular to the scanning direction.

The photoacoustic transducer 4b is a device in which the electromechanical transducers are two-dimensionally arranged. Examples of the electromechanical transducer include a transducer using a piezoelectric phenomenon, a transducer using optical resonance, and a transducer using a change in capacity. Any detector may be employed as the electromechanical transducer as long as the detector can detect an acoustic wave. In a case where sizes of detection targets vary widely, bands of generated photoacoustic waves are also widened, and hence a required transducer favorably has a wide detection band. In consideration of the above-mentioned aspect, an electrostatic capacity type ultrasonic transducer, which has actively been studied in recent years, is one of most suitable transducers for the object of the present invention. Alternatively, when a device in which plural transducers having different detection bands are combined is employed, the same effect can be expected.

The ultrasonic probe according to this embodiment is manufactured in the following manner. First, the ultrasonic transducer 4a (one-dimensional array transducer) and the photoacoustic transducer 4b (two-dimensional array transducer) are manufactured by a method similar to the conventional method. The method includes cutting out a piezoelectric transducer; fixing the transducer to a backing material; dicing the transducer; bonding an acoustic matching layer; and leading out a wiring portion. In addition, an acoustic lens is attached to the ultrasonic transducer.

The ultrasonic transducer and the photoacoustic transducer are arranged with a space therebetween, and then fixed by molding. After that, the ultrasonic transducer and the photoacoustic transducer are fit into a housing, whereby the ultrasonic probe is completed.

The acoustic matching layer, the backing, and the wiring are provided on an upper surface and a lower surface of each of the transducers, and the acoustic lens is provided on the upper surface of the ultrasonic transducer. Those components are omitted in FIGS. 1A and 1B.

The ultrasonic transducer 4a and the photoacoustic transducer 4b have a positional relation in which the ultrasonic transducer 4a is provided in parallel to any one of four sides of the photoacoustic transducer 4b which is two-dimensionally arrayed. In this embodiment, the two array devices are housed in one probe case 30. Alternatively, a probe case that houses the ultrasonic transducer 4a and a probe case that houses the photoacoustic transducer 4b may be provided to form one probe as a whole. In this case, the two array devices are only required to be on the same plane and may be located with a certain space therebetween.

Figure 2:
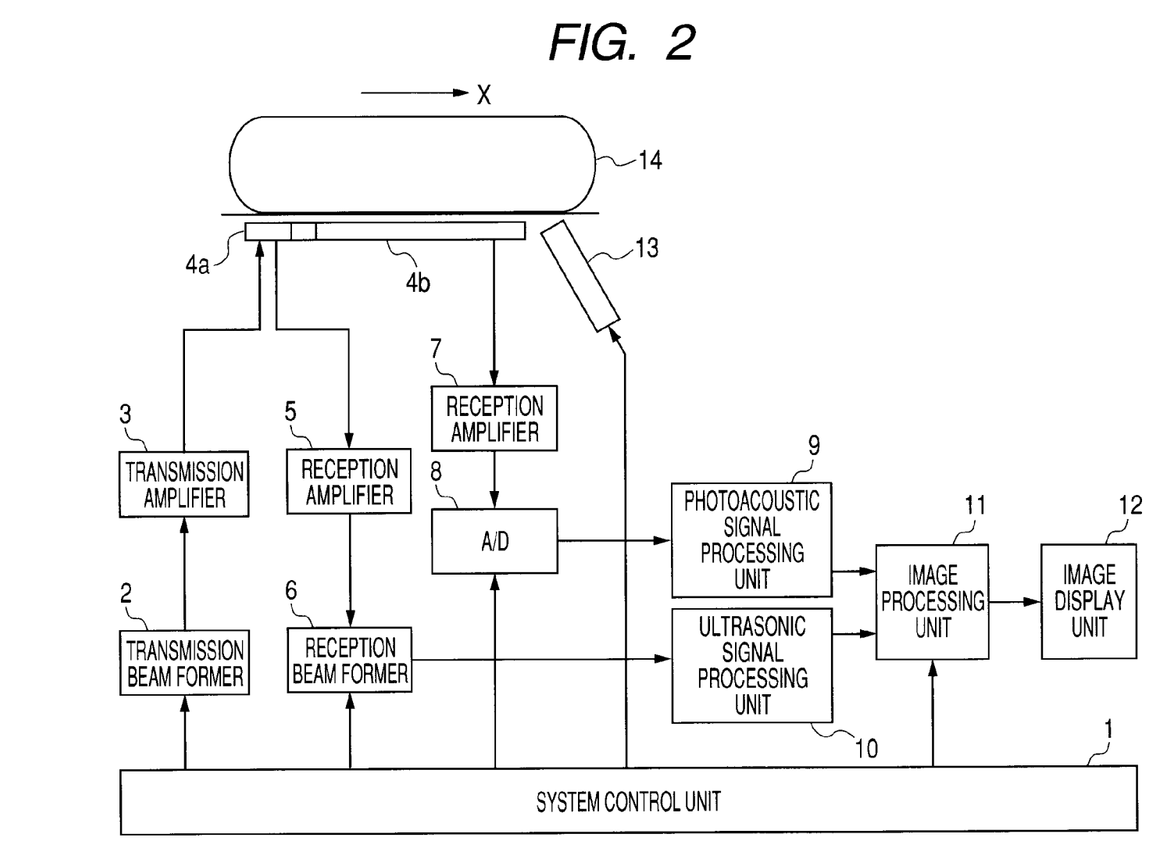
FIG. 2 is a diagram illustrating a configuration of an inspection object imaging apparatus including the ultrasonic probe according to the embodiment of the present invention.

FIG. 2 is a block diagram illustrating an inspection object imaging apparatus using the ultrasonic probe according to this embodiment. In order to transmit an ultrasonic wave from the ultrasonic transducer 4a, an ultrasonic signal is generated through a system control unit 1, a transmission beam former 2, and a transmission amplifier 3, and then a voltage is applied to the ultrasonic transducer 4a. The transmitted ultrasonic wave is reflected on an inspection object 14 and received by the ultrasonic transducer 4a. The received ultrasonic signal, each of the signals of the respective devices in the ultrasonic probe, is subjected to phasing addition through a reception amplifier 5 and a reception beam former 6. The reception beam former 6 performs analog-digital conversion, delay, and weighting control. Then, the ultrasonic signal is detected and converted into a luminance signal by an ultrasonic signal processing unit 10, and is accumulated in an image memory within an image processing unit 11.

On the other hand, a photoacoustic wave is detected in the following manner. A light source 13 irradiates the inspection object 14 with pulse laser light. The pulse laser light is emitted by transmitting a drive signal from the system control unit 1 to the light source 13. When the inspection object 14 is irradiated with the pulse laser light, a detection target inside the inspection object 14, such as hemoglobin, absorbs energy of the laser light. The temperature of the detection target rises in accordance with the amount of the absorbed energy. As a result of the temperature rise, the detection target momentarily expands to generate an elastic wave (photoacoustic wave). The generated photoacoustic wave is received by the photoacoustic transducer 4b, passes through a reception amplifier 7 and an analog-digital converter 8, and then is subjected to an image reconstruction processing by a photoacoustic signal processing unit 9. The reconstructed photoacoustic signal is accumulated as a luminance signal in the image memory within the image processing unit 11.

Then, the image processing unit 11 superimposes the accumulated ultrasonic signals on the accumulated photoacoustic signals followed by image display by an image display unit 12.

Next, a method of acquiring three-dimensional signals of an ultrasonic signal and a photoacoustic signal with the use of the ultrasonic probe according to this embodiment is described. As described above, the one-dimensional array is employed for the ultrasonic transducer and the two-dimensional array is employed for the photoacoustic transducer, and hence, in order to acquire volume data with the use of the ultrasonic probe according to this embodiment, scanning is performed with the ultrasonic probe.

Figure 3:
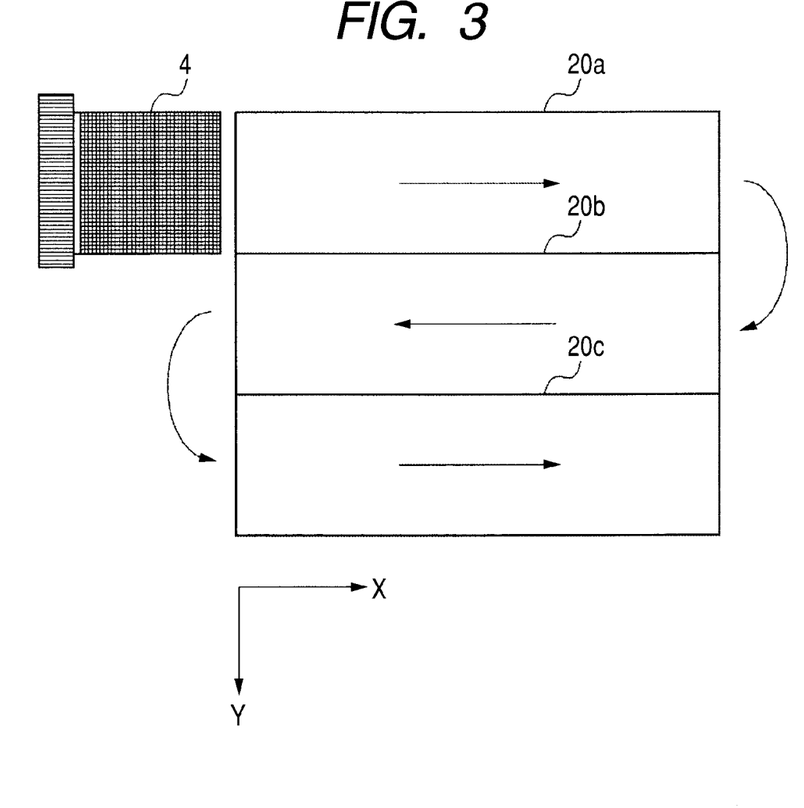
FIG. 3 is a diagram for describing a signal collection method using the ultrasonic probe according to the embodiment of the present invention.

FIG. 3 is a conceptual diagram of scanning performed with the ultrasonic probe according to this embodiment, and illustrates scanning areas 20a, 20b, and 20c. In the scanning, the ultrasonic probe is moved in the second direction (X direction of FIG. 3) in which the ultrasonic transducer 4a and the photoacoustic transducer 4b are arranged. When the scanning of the scanning area 20a is finished, the ultrasonic probe is moved in a longitudinal direction (Y direction of FIG. 3) by a stripe width of the scanning area and then is moved over the scanning area 20b in the opposite direction. The above-mentioned scanning is repeatedly performed, whereby signals of an entire inspection area are acquired.

The following three patterns of methods are conceivable for the scanning: (a) a method in which a photoacoustic signal is acquired during a stage suspension period and an ultrasonic signal is acquired during a stage moving period; (b) a method in which a photoacoustic signal and an ultrasonic signal are both acquired during the stage suspension period; and (c) a method in which a photoacoustic signal and an ultrasonic signal are both acquired during the stage moving period. The same signals can be acquired by any one of the above-mentioned methods.

First, in the method (a) in which the photoacoustic signal is acquired during the stage suspension period and the ultrasonic signal is acquired during the stage moving period, the pulse laser is irradiated during the stage suspension period to acquire the photoacoustic signal. After that, the ultrasonic signals are continuously transmitted and received during the stage moving period, and a process of acquiring a slice image at each position is repeated. In this case, for example, the length of the photoacoustic transducer 4b in the scanning direction (X direction) is taken as one step width, and one set of pulse laser irradiation, photoacoustic signal detection and moving by one-step width is repeated. When the transducer 4 is moved by the one-step width, the ultrasonic wave is acquired using the ultrasonic transducer 4a. The step width of the transducer 4 may be determined based on a range in which the photoacoustic transducer 4b can detect the photoacoustic wave. In other words, in a case where a range in the X direction in which the photoacoustic transducer 4b can detect a photoacoustic wave is narrow, the step width of the transducer 4 is made narrow.

Next, in the method (b) in which the photoacoustic signal and the ultrasonic signal are both acquired during the stage suspension period, the pulse laser is first irradiated during the stage suspension period to acquire the photoacoustic signal. After that, the ultrasonic signals are transmitted and received, and a slice image is acquired. Those procedures may be performed in the opposite order. After the stage is moved, the same process is repeated. In this method, the amount of one stage moving corresponds to that of such an extent that the volume data can be created from the slice image generated by the ultrasonic signal, that is, that of the same order of resolution of the slice image. In this method, when the information on the inspection object can be obtained only by acquiring the image information at one position, the image can be obtained while the stage is suspended without being moved.

In the method (c) in which the photoacoustic signal and the ultrasonic signal are both acquired during the stage moving period, the pulse laser irradiation, the photoacoustic signal acquisition, and the transmission and reception of the ultrasonic signal are performed during the stage moving period. In this case, the pulse laser is emitted at an operating frequency of ten to several tens hertz, and the transmission and reception of the ultrasonic signal are performed at an operating frequency on the order of kilohertz. Therefore, each data is acquired with a duty ratio therebetween of approximately 100.

As described above, the stripe width (length in Y direction) of the scanning by the transducer 4 is equal to the width of the photoacoustic transducer 4b (two-dimensional array) which is the photoacoustic probe. This is because luminance signals within the volume area are calculated based on the photoacoustic signals at all positions when an image is reconstructed from the photoacoustic signals. Specifically, in a case where the stripe width is thicker than the width of the photoacoustic transducer 4b, there is a portion which is not inspected. Conversely, in a case where the width of the photoacoustic transducer 4b is thicker than the stripe width, there are devices which are not used. Accordingly, an optimum condition for each width is such that the stripe width and the width of the photoacoustic transducer 4b are made equal to each other.

On the other hand, when the ultrasonic transducer 4a which is the ultrasonic probe acquires the ultrasonic signal in the stripe, the length of the one-dimensional array of the ultrasonic transducer 4a needs to be made longer than the stripe width.

Figure 4:
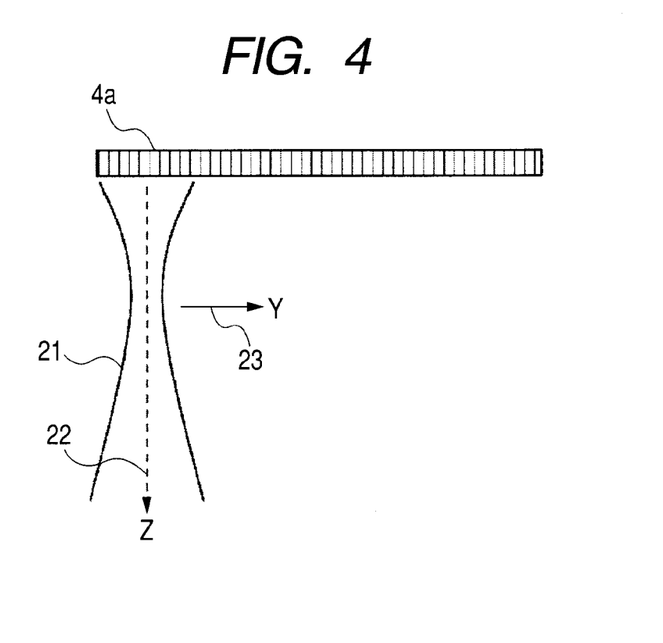
FIG. 4 is a diagram illustrating a beam shape of the ultrasonic transducer according to the present invention.

With reference to FIG. 4, a linear scanning of an ultrasonic beam by the ultrasonic transducer 4a is described. FIG. 4 is a diagram illustrating the ultrasonic transducer 4a viewed from the scanning direction (X direction) of the transducer 4. In general, one transmission and one reception of an ultrasonic beam 21 are performed by multiple devices. Therefore, a beam center 22 in a Z direction of FIG. 4 inevitably lies inside with respect to an end surface of the probe. Accordingly, an ultrasonic image obtained by the ultrasonic transducer 4a in a beam scanning direction 23 (Y direction) is narrower than the array width of the ultrasonic transducer 4a by an aperture width used for the beam transmission and reception. Therefore, when the scanning is performed using a linear probe having the same width as the stripe width, there is a portion in which signals are not acquired between the stripes.

When the aperture for the beam transmission and reception is made smaller or when a particular method such as steering is used, imaging is possible also on the end surface of the probe. However, in a case of using those methods, methods of forming a beam are different between the center of the probe and the end surface thereof, which causes nonuniformity in the resolution and image quality.

Therefore, in this embodiment, the array length of the ultrasonic transducer 4a is made longer than the stripe width, whereby loss of the ultrasonic signals between the stripes can be avoided.

In view of the above, in the transducer 4 according to this embodiment, the length of the ultrasonic transducer 4a in the direction perpendicular to the scanning direction may be set to be longer than the length of the photoacoustic transducer 4b in the direction perpendicular to the scanning direction. The length of the ultrasonic transducer 4a in the direction perpendicular to the scanning direction may be made longer at respective longitudinal ends thereof by one half the length (aperture width) of the device used for transmitting and receiving an ultrasonic wave. As a result, when the increased lengths of the respective longitudinal ends are added, the total length of the ultrasonic transducer 4a becomes longer by a length equal to the aperture width. In general, the aperture of an ultrasonic beam is formed of several tens of devices, and hence the array length of the ultrasonic transducer 4a may be set to be longer than the stripe width by a length corresponding to several tens of devices.

Figure 5:
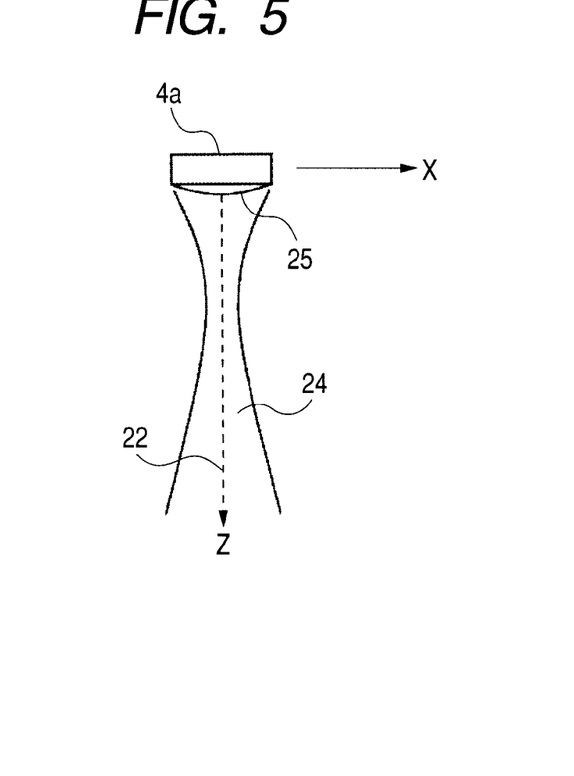
FIG. 5 is a diagram illustrating a beam shape of the ultrasonic transducer in a height direction thereof according to the present invention.

FIG. 5 illustrates a state in which a beam generated by the ultrasonic transducer 4a is focused in a depth direction of the inspection object. The ultrasonic transducer 4a for transmitting and receiving an ultrasonic signal includes an acoustic lens 25 on an entire surface thereof in order to focus a beam also in a height direction thereof (Z direction). Similarly to the above-mentioned lateral direction beam, an ultrasonic beam is focused while following a locus 24 of FIG. 5. However, a range of acquiring an ultrasonic signal has a certain distance from immediately below the probe, and hence it is difficult to prevent the ultrasonic beam from spreading. The spreading of the ultrasonic beam in this case depends on focus conditions and lens conditions, and may be substantially equal to the height of the probe or may be wider than the height of the probe.

Figure 6:
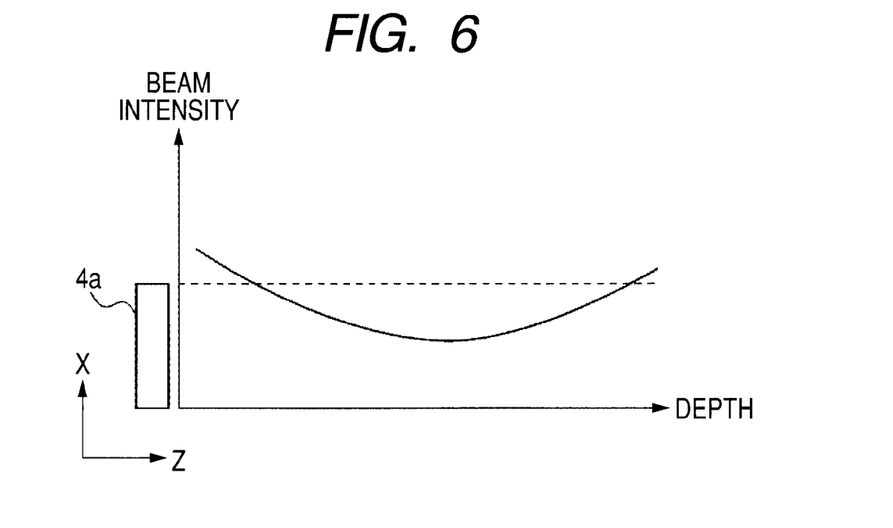
FIG. 6 is a graph illustrating a relation between the ultrasonic probe and a beam thickness of the ultrasonic transducer in the height direction according to the present invention.

FIG. 6 illustrates a form of the beam generated by the ultrasonic transducer 4a. As illustrated in FIG. 6, the width of the beam generated by the ultrasonic transducer 4a exceeds the width of the ultrasonic transducer 4a in a shallower portion and a deeper portion in the depth direction of the inspection object.

Meanwhile, according to the present invention, the photoacoustic transducer 4b is provided in a portion close to the ultrasonic transducer 4a. Therefore, there is a fear that an interference (crosstalk) between the ultrasonic wave from the ultrasonic transducer 4a and the photoacoustic wave detected by the photoacoustic transducer 4b may be generated. Accordingly, in this embodiment of the present invention, an interspace is provided between the ultrasonic transducer 4a and the photoacoustic transducer 4b, whereby the crosstalk can be prevented. The size of the interspace depends on the width of the ultrasonic transducer 4a, the focus conditions, and the like. For example, a calculation reveals that there is no problem when the ultrasonic transducer 4a and the photoacoustic transducer 4b are separated from each other in the scanning direction by a distance corresponding to 20% or more of the length of the ultrasonic transducer 4a in the scanning direction.

With the use of the ultrasonic probe described above, all ultrasonic signals and photoacoustic signals can be acquired within the scanning range. In the mode described above, the one-dimensional array probe is employed for acquiring the ultrasonic signal, but the present invention is not limited thereto. Probes generally referred to as 1.25-dimensional array probe, 1.5-dimensional array probe, and 1.75-dimensional array probe, in which devices are further divided in a direction orthogonal to the array direction, may be employed.

The 1.25-dimensional array probe, in which the devices are divided into an odd number of parts in the direction orthogonal to the array direction, has an aperture control function by switching the other devices than a central device. The 1.5-dimensional array probe, in which the devices are divided in the direction orthogonal to the array direction as in the case of the 1.25-dimensional array probe, is capable of independently controlling a central device and symmetrical devices. The 1.75-dimensional array probe, in which the devices are divided in the direction orthogonal to the array direction as in the case of the 1.25-dimensional array probe, is capable of independently controlling all devices in the direction orthogonal to the array direction. Each of the 1.25-dimensional, 1.5-dimensional, and 1.75-dimensional array probes is mounted for improving focusing and steering functions in the direction orthogonal to the array direction, and the same effect can be obtained by the above-mentioned array probes as in the case where the one-dimensional array probe is employed.

In the mode described above, the one-dimensional array probe is employed for acquiring the ultrasonic signal and the two-dimensional array probe is employed for acquiring the photoacoustic signal. However, the one-dimensional array probe may be employed for acquiring both the ultrasonic signal and the photoacoustic signal. In this case, for the relationship of the array lengths of the probes, similarly to the above-mentioned mode, the array length of an array probe for acquiring the ultrasonic signal is set to be longer than the array length of an array probe for acquiring the photoacoustic signal, thereby obtaining the same effect.

Second Embodiment: Photoacoustic-Ultrasonic System

Figure 7A:
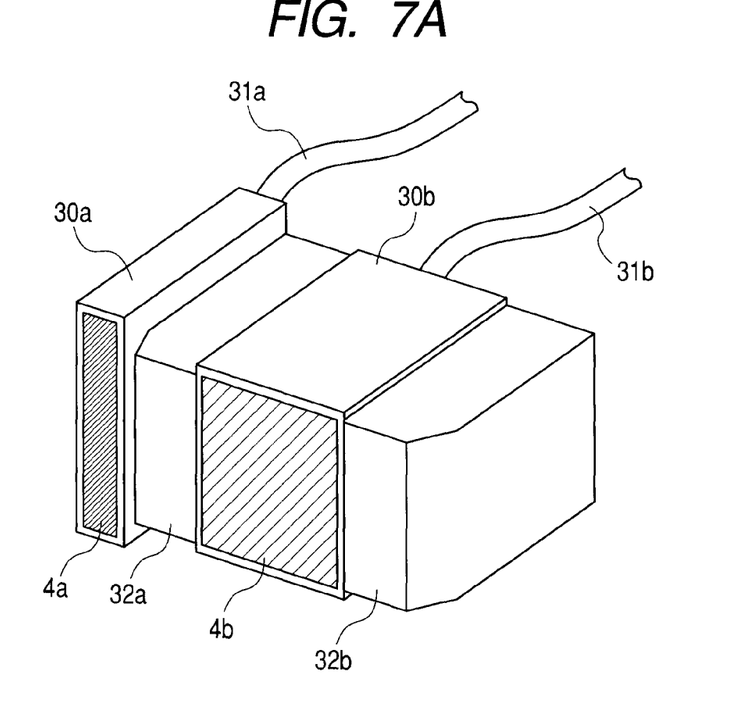
FIG. 7A is a perspective view illustrating a photoacoustic-ultrasonic system including an ultrasonic probe and an optical system according to another embodiment of the present invention.

Next, a photoacoustic-ultrasonic system in which an optical system is combined with an ultrasonic probe is described. FIG. 7A is a perspective view illustrating the photoacoustic-ultrasonic system including the ultrasonic probe and the optical system according to this embodiment.

A first probe for transmitting and receiving an ultrasonic wave includes a probe case 30a, a cable 31a, and a transducer 4a. A second probe for receiving a photoacoustic wave includes a probe case 30b, a cable 31b, and a transducer 4b. The transducer 4a is a first array device capable of transmitting and receiving the ultrasonic wave. The transducer 4b is a second array device capable of receiving the photoacoustic wave. A one-dimensional (linear) array is employed for the ultrasonic transducer 4a while a two-dimensional array is employed for the photoacoustic transducer 4b.

An optical prism 32a is provided in an interspace between the ultrasonic transducer 4a and the photoacoustic transducer 4b. The optical prism 32a serves as an optical system for introducing pulse light emitted from a light source into an inspection object. An optical prism 32b may similarly be provided on a side of the second probe, which is opposite to the optical prism 32a, so as to guide light from both sides of the photoacoustic-ultrasonic system. This is because a target region may need to be irradiated as uniformly as possible due to the fact that the intensity of the generated photoacoustic wave largely depends on an irradiation intensity of laser.

Figure 7B:
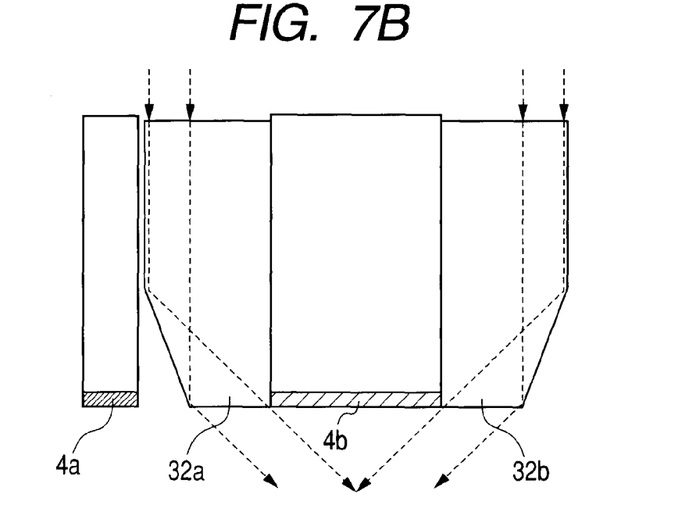
FIG. 7B is a cross-sectional view of the photoacoustic-ultrasonic system, which illustrates incidence of light.

FIG. 7B is a cross-sectional view of the photoacoustic-ultrasonic system according to this embodiment, which illustrates incidence of light. The light enters a sample as indicated by a broken line of FIG. 7B. The light from the light source (not shown) is first guided in a direction perpendicular to a plane on which the two array devices 4a and 4b are provided. The traveling direction of the guided light is changed by the optical prisms 32a and 32b, whereby the light is emitted toward below the second array device 4b.

The optical prism 32a is provided between the two probes in this manner. Accordingly, even in a case where the two-dimensional array device 4b is used, light can be effectively applied to the photoacoustic transducer 4b which detects the photoacoustic wave. In addition, the two array devices 4a and 4b naturally need to be spaced apart from each other, and hence the crosstalk described in the first embodiment can be prevented.

The space between the two array devices 4a and 4b is described. It is understood that, in order to realize uniform irradiation as described above, the thickness of an optical path needs to be a half or more of the width of the photoacoustic transducer 4b for each side irrespective of an irradiation angle of laser. Therefore, an interspace having a size equal to at least a half of the width of the photoacoustic transducer 4b needs to be provided between the ultrasonic transducer 4a and the photoacoustic transducer 4b. In other words, the two array devices 4a and 4b may be separated from each other in the second direction by a distance corresponding to 50% or more of the length of the second array device in the second direction.

A method of manufacturing the photoacoustic-ultrasonic system according to this embodiment is the same as that of the first embodiment, and hence the description thereof is omitted.

In the mode described above, the optical prisms are provided on both sides of the second probe. However, when optical prisms are provided so as to surround a probe, a more favorable irradiation amount distribution can be obtained.

EXAMPLE

Hereinafter, in this example, a case where the probe according to the present invention is used for a mammary examination is specifically described. In the mammary examination, it is sufficient that an ultrasonic signal and a photoacoustic signal for up to a depth of 4 cm are acquired. The probe used in this case is the probe of FIGS. 1A and 1B which is used in the description above.

A laser light intensity allowable to be applied to a human body is 100 mJ/cm$^2$, and hence a range in which a sufficient photoacoustic signal can be acquired is 4 cm in depth and 4 cm in width. Accordingly, one side of a photoacoustic probe was set to 4 cm. Accordingly, one side of the photoacoustic probe was set to 4 cm. The device pitch was set to 2 mm in consideration of probe sensitivity and a frequency of 1 MHz to be used, whereby a two-dimensional array probe including 400 devices was formed. An electrostatic capacity type ultrasonic transducer having a band width of 130% was used as the two-dimensional array probe because the two-dimensional array probe is required to detect targets having various sizes.

On the other hand, with regard to an ultrasonic probe, beam forming was performed with a 32-device aperture in order to sufficiently converge beams. Therefore, the ultrasonic probe is longer than the photoacoustic probe by 16 devices on each of the left and right sides. The total number of devices was set to 192, the device pitch was set to 0.25 mm, the center frequency was set to 10 MHz, and the array length was set to 48 mm. Further, an acoustic lens which is formed on a surface of the ultrasonic probe had a radius of R8. The beam formed under the above-mentioned conditions spreads to 7 mm in the vicinities of the ultrasonic probe and the vicinities of a depth of 4 cm, and hence an interspace between the ultrasonic probe and the photoacoustic probe was set to 1 mm.

Considering that the mamma is scanned using the above-mentioned probes, five strips each having a size of 4 cm×20 cm were formed because the scanning region is 20 cm×20 cm and the stripe width is 4 cm. The scanning with the probes was performed in a step-and-repeat manner. Laser was applied while the probes were suspended, and the photoacoustic signal was acquired by the two-dimensional array probe. Then, while the probes were moving, the ultrasonic signal was acquired by the one-dimensional array probe, and an ultrasonic image of each slice surface was generated and stored as volume data after being subjected to an interpolation processing.

After the scanning of an entire target surface is finished, the image is reconstructed using the photoacoustic signal. A photoacoustic image generated by the reconstruction is accumulated as volume data and superimposed on the ultrasonic image. The resultant image is displayed on a screen. The photoacoustic signal and the ultrasonic signal can be superimposed on each other by the above-mentioned method, with the result that information containing a morphologic image and a functional image can be provided to a user.

In this example, the 32-device aperture for an ultrasonic beam was adopted. When the size of the aperture is changed according to required beam resolution or a required beam forming method, the same effect can also be obtained.

The photoacoustic-ultrasonic system illustrated in FIGS. 7A and 7B can also be used for the mammary examination. In this case, the interspace between the ultrasonic probe and the photoacoustic probe needs to be at least 1.4 mm. On the other hand, in consideration of an incidence angle of 45 degrees and 2 cm which is one half the length of one side of the photoacoustic probe of 4 cm, the necessary thickness of a prism is 2.83 cm, and hence the space between the probes was set to 2.83 cm.

The present invention is not limited to the above embodiments and various changes and modifications can be made within the spirit and scope of the present invention. Therefore to apprise the public of the scope of the present invention, the following claims are made.

This application claims the benefit of Japanese Patent Applications No. 2008-159314, filed Jun. 18, 2008, and No. 2009-136365, filed Jun. 5, 2009, which are hereby incorporated by reference herein in their entirety.

The invention claimed is:

1. An ultrasonic probe, comprising:
   a first array device capable of transmitting and receiving an ultrasonic wave; and
   a second array device capable of receiving a photoacoustic wave,
   wherein the first array device includes a plurality of electromechanical transducers arranged in a first direction; the second array device includes a plurality of electromechanical transducers arranged in a two-dimensional manner; and
   the first array device and the second array device are provided on the same plane and in a second direction perpendicular to the first direction; and
   wherein the length of the first array device in the first direction is longer than the longest length in the first direction of the second array device.

2. An ultrasonic probe according to claim 1, wherein the first array device and the second array device are separated from each other in the second direction by a distance corresponding to 20% or more of the length of the first array device in the second direction.

3. An ultrasonic probe according to claim 1, wherein the first array device and the second array device are separated from each other in the second direction by a distance corresponding to 50% of the length of the second array device in the second direction.

4. An ultrasonic probe according to claim 1, wherein the second direction corresponds to a scanning direction in which the first array device and the second array device are scanned.

5. An ultrasonic probe according to claim 1, wherein the second array device comprises an electrostatic capacity type ultrasonic transducer.

6. An ultrasonic probe according to claim 1, wherein in the first direction a difference between the length of the first array device and the longest length in the first direction of the second array device is not less than a width of an aperture used for transmission and reception of a beam of the ultrasonic wave by means of the first array device.

7. A photoacoustic-ultrasonic system, comprising:
   an optical system for introducing light emitted from a light source into an inspection object; and the ultrasonic probe according to claim 1,
wherein the optical system is provided in an interspace between the first array device and the second array device.

8. A photoacoustic-ultrasonic system according to claim 7, wherein the optical system is provided so that light guided between a first probe including the first array device and a second probe including the second array device in a direction perpendicular to the plane is emitted from the interspace between the first array device and the second array device toward below the second array device.

9. A photoacoustic-ultrasonic system according to claim 8, wherein the optical system is provided so that light is guided from both sides of the second probe.

10. An inspection object imaging apparatus, comprising:
a light source for generating pulse light;
the ultrasonic probe according to claim 1; and
a system control unit for controlling the light source and the ultrasonic probe to form an image,
wherein the system control unit forms an image based on morphologic information of the inside of an inspection object by using the first array device and forms an image based on functional information of the inside of the inspection object by using the light source and the second array device.

11. An inspection object imaging apparatus according to claim 10, wherein the first array device transmits and receives an ultrasonic wave having a frequency higher than the frequency of an ultrasonic wave received by the second array device.

12. An inspection object imaging apparatus according to claim 10,
wherein the first array device transmits and receives an ultrasonic wave having a frequency of 7 to 12 MHz; and
wherein the second array device receives an ultrasonic wave having a frequency of 1 to 4 MHz.

13. An ultrasonic probe, comprising:
a first array device capable of transmitting and receiving an ultrasonic wave; and
a second array device capable of receiving a photoacoustic wave,
wherein
the first array device includes a plurality of electromechanical transducers arranged in a first direction;
the second array device includes a plurality of electromechanical transducers arranged in a two-dimensional manner;
the first array device and the second array device are provided on the same plane and in a second direction perpendicular to the first direction;
the length of the first array device in the first direction is longer than the length of the second array device in the first direction; and
in the first direction, a difference between the length of the first array device and the length of the second array device is not less than a width of an aperture for transmission and reception of a beam of the ultrasonic wave used by the first array device.

14. An ultrasonic probe according to claim 13, wherein the second array device comprises an electrostatic capacity type ultrasonic transducer.

15. An ultrasonic probe according to claim 13, wherein the first array device and the second array device are separated from each other in the second direction by a distance corresponding to 20% or more of the length of the first array device in the second direction.

16. An ultrasonic probe according to claim 13, wherein the second direction corresponds to a scanning direction in which the first array device and the second array device are scanned.

17. A photoacoustic-ultrasonic system, comprising:
an optical system for introducing light emitted from a light source into an inspection object; and
the ultrasonic probe according to claim 13.

18. An inspection object imaging apparatus, comprising:
a light source for generating pulse light;
the ultasonic probe according to claim 13; and
a system control unit for controlling the light source and the ultrasonic probe to form an image,
wherein the system control unit forms an image based on morphologic information of the inside of the inspection object by using the first array device and forms an image based on functional information of the inside of the inspection object by using the light source and the second array device.

19. An inspection object imaging apparatus according to claim 18, wherein the first array device transmits and receives an ultrasonic wave having a frequency higher than the frequency of an ultrasonic wave received by the second array device.

20. A photoacoustic-ultrasonic system, comprising:
an optical system for introducing light emitted from a light source into an inspection object; and
an ultrasonic probe, comprising:
a first array device capable of transmitting and receiving an ultrasonic wave; and
a second array device capable of receiving a photoacoustic wave,
wherein the first array device includes a plurality of electromechanical transducers arranged in a first direction; the second array device includes a plurality of electromechanical transducers arranged in a two-dimensional manner; and the first array device and the second array device are provided on the same plane and in a second direction perpendicular to the first direction;
wherein the optical system is provided in an interspace between the first array device and the second array device, and
wherein the optical system is provided so that light guided between a first probe including the first array device and a second probe including the second array device in a direction perpendicular to the plane is emitted from the interspace between the first array device and the second array device toward below the second array device.

* * * * *